United States Patent [19]

Cox et al.

[11] 4,412,006
[45] Oct. 25, 1983

[54] METHOD FOR DETERMINATION OF NITRATE AND/OR NITRITE

[75] Inventors: Robert D. Cox, Austin, Tex.; Clyde W. Frank, Iowa City, Iowa

[73] Assignee: University of Iowa Research Foundation, Iowa City, Iowa

[21] Appl. No.: 361,586

[22] Filed: Mar. 25, 1982

Related U.S. Application Data

[63] Continuation of Ser. No. 174,690, Aug. 1, 1980, abandoned.

[51] Int. Cl.³ .............................................. G01N 21/76
[52] U.S. Cl. .................................. 436/110; 436/172; 436/175; 422/52
[58] Field of Search ........... 23/230 PC, 232 C, 232 E, 23/927; 422/52; 423/405, 402; 436/110, 172, 436/177, 175

[56] References Cited

U.S. PATENT DOCUMENTS

| | | | |
|---|---|---|---|
| 2,245,550 | 6/1941 | Andrussow et al. | 423/402 |
| 3,366,574 | 1/1968 | Chleck | 422/52 |
| 3,647,387 | 3/1972 | Benson et al. | 23/232 E X |
| 3,730,686 | 5/1973 | Breitenbach et al. | 423/405 X |
| 3,877,875 | 4/1975 | Jones et al. | 23/230 PC |
| 3,973,914 | 8/1976 | Heusden | 422/52 |
| 3,996,005 | 12/1976 | Topol | 23/232 E X |
| 3,996,339 | 12/1976 | Falkenburg | 23/232 E X |
| 4,073,866 | 2/1978 | Yamaki et al. | 423/405 |
| 4,221,761 | 9/1980 | Bullens et al. | 23/232 E X |
| 4,236,895 | 12/1980 | Stahl | 23/232 E X |

FOREIGN PATENT DOCUMENTS

| | | | |
|---|---|---|---|
| 52-58987 | 5/1977 | Japan | 23/927 |
| 7608957 | 2/1978 | Netherlands | 423/405 |

*Primary Examiner*—Kenneth M. Schor
*Attorney, Agent, or Firm*—Zarley, McKee, Thomte, Voorhees & Sease

[57] ABSTRACT

A technique of determination of nitrate-nitrite content of a test sample, without also determining additional nitrogen content. The technique is highly selective and sensitive, to the parts per billion level. The nitrate-nitrite content of a sample is reduced to nitric oxide which is determined via its chemiluminescence reaction with ozone. Nitrite is selectively reduced under mild conditions and the total nitrate-nitrite content is determined by stronger reduction conditions. Specific reducing agents to be used in combination with the chemiluminescence reaction are also provided.

4 Claims, No Drawings

METHOD FOR DETERMINATION OF NITRATE AND/OR NITRITE

This is a continuation of application Ser. No. 174,690, filed Aug. 1, 1980, now abandoned.

BACKGROUND OF THE INVENTION

Nitrate and nitrite are anions occuring in a wide array of natural systems. In the environment both species are produced in the nitrification process, in which ammonia is oxidized by certain soil bacteria. Nitrate occurs in abundance in part because of the use of nitrate salts as fertilizers. Also, nitrite results through the reduction of nitrate by denitrification bacteria. This process is thought to be important in the occurrence of nitrite in the human intestine. Humans are exposed to nitrates and nitrites through the injection of vegetables, water and cured meats. Nitrite in high levels can be fatal to infants causing a condition known as methemoglobinemia.

It can therefore be seen that there is a continuing need for a selective analytical test system which determines nitrate and nitrite content. This is even more true as continuing biological and medical research shows increasing evidence of the physiological activity of these anions with respect to continued human exposure. Also, there is a continuing need for a sensitive and selective system of nitrate and nitrite analysis which can be conducted in the presence of turbid and colored fluids such as some biological fluids like urine and blood.

Then too, there is a need for an analytical technique which is specific to the nitrate-nitrite anions. That is to say, it determines only nitrate and/or nitrite without also determining total nitrogen content.

Yet another continuing need is for a system which can detect nitrate and nitrite even at the parts per billion level.

In the past most analytical techniques have not been able to differentiate between nitrate and nitrite and have simply determined total nitrogen content. Some techniques which have previously been used for nitrate and nitrite determination are the following. The most common method for nitrite involves the reaction of nitrite with sulfanilamide in acidic solution to yield a diazonium salt which is coupled with an aromatic amine to produce a highly colored azo compound. Methods for the spectrophotometric determination of nitrate are generally based on nitration of a phenolic type compounds, oxidation of an organic compound by nitrate, or reduction of nitrate to nitrite and determination via the sulfanilamide method. These methods have been reported to be subject to various interferences, thus requiring elaborate clean-up procedures when working with biological media. Ion chromatography has been applied to the determination of nitrate and nitrite in environmental samples. Although this method is more selective than those based on colorimetry, it is limited by a lack of sensitivity.

Both nitrate and nitrite have been determined volumetrically or manometrically by reduction to various gaseous species. An ultraviolet absorption method for nitrate by reduction to ammonia has been published. Methods have also been described in which nitrate and nitrite were determined by thermal reduction to nitric oxide followed by chemiluminescence detection. In general the chemical reduction of nitrate required highly acidic conditions except when vanadium (II) was used as a reducing agent. Although volumetric methods are applicable only to samples containing relative large amounts of nitrate or nitrite, under the appropriate kinetic conditions the reactions are presumed to be applicable to much lower amounts of nitrate or nitrite.

None of these systems have been sufficient to fulfill the needs earlier mentioned herein.

It is therefore a primary objective of the present invention to provide a technique of determination of nitrate-nitrite at extremely low levels, which is highly selective in that it determines only nitrate and nitrite without also determining total nitrogen content, which can be quickly, efficiently and easily run, which can be run on extremely small samples, which can be run on fluid samples of high turbidity and color such as urine and blood, and which, if run in a specific sequence, can differentiate between nitrite and nitrate. This is accomplished by first reducing and determining nitrite with a weak reducing agent under mild conditions and thereafter determining the nitrate under stronger reducing conditions.

The manner of fulfilling each of the needs, goals and objectives of this invention will be set forth hereinafter.

SUMMARY OF THE INVENTION

A method of determination of the nitrate-nitrite content of a test sample. The method is highly sensitive, selective, quick to run, and is essentially free from interference of other materials. The method involves reducing the nitrate-nitrite content of a test sample to nitric oxide with an acidic solution of a reducing agent which is selective to this reduction without also reducing other nitrogen containing substances; and thereafter, reacting the produced nitric oxide with ozone in a chemiluminescent reaction, and determining the magnitude of the chemiluminescent reaction to indicate the quantity of nitrate-nitrite in the sample. Also, an important part of the invention are the preferred reducing agents used in the specific analytical detection method.

DETAILED DESCRIPTION OF THE INVENTION

As heretofore mentioned, the method of this invention has numerous advantages, amongst which are selectivity, sensitivity and speed. As used in this disclosure, "selectivity" refers to the fact that the method is specific to determining of nitrate-nitrite without also determining total nitrogen content, or other nitrogen compounds. "Sensitivity" refers to the fact that it can determine nitrate-nitrite content of small samples and also determine it at very low levels, even at the parts per billion level.

In accordance with the technique of the present invention, the test sample must first, of course, be placed in a form suitable for the methodology. In particular, if the composition is not liquid, it must be solubilized or converted to a liquid solution containing the nitrate-nitrite. Normally, it is simply sufficient if the solid material, if that is what is being tested, is simply slurried with vigorous stirring with water. This is normally sufficient to extract the nitrate and nitrite anions which are highly water soluble.

After the solubilization of the test sample, it is now ready for use in the method of the present invention.

The now liquid (solution) nitrate-nitrite test sample is next reacted with an acidic solution of a reducing agent which is selective to reduction of nitrate and nitrite without also reducing other nitrogen containing substances. While there are a variety of reactants capable of reducing nitrate-nitrite, it must be remembered that in accordance with the process of the present invention, this reduction is here coupled with chemiluminescence detection. Thus, since chemiluminescence detection is also involved, the criteria used for the choice of reducing agents greatly limited the list of possibilities. Reducing agents which can be used must meet several requirements. First the species produced by the reduction must be nitric oxide. Secondly, the reaction must be rapid and quantitative at low nitrate and nitrite levels. Thirdly, the reagent should be of very low volatility.

Using these criteria and after testing many reducing agents, it was found that Fe(II) with Mo(VI) catalyst, or Ti(III) provided the desired properties for the reduction of nitrate to nitric oxide at the parts per billion level. For the nitrite reaction, it can be selectively determined, even as opposed to nitrate, by iodide ion in a weakly acidic medium. It can also be determined, along with nitrate, if one does not desire to distinguish between the two by use of the stronger reducing agents, previously mentioned.

It can be seen that the stronger reducing agents which have been selected are all transition metal ions. In particular, the ferrous ion (II) in the presence of Mo(VI) catalyst or the titanium (III) ion, have been found as very effective reducing reagent systems. These are strong reducing reagents since a strong agent has been found needed to reduce the nitrate anion to nitric oxide.

It has also been found that hydroquinone in the presence of a molybdenum (VI) catalyst will also work. Both the transition metal ion systems and the hydroquinone system have been found most effective in a highly acidic solution, most preferably a concentrated sulfuric acid solution. It is conceivable that other strong acids would work, but sulfuric is preferred for two reasons; the reaction is faster and one may use advantageously the heat of mixing as it mixes with water.

The transition metal ion reduction systems and the hydroquinone reduction system just previously mentioned herein, both have the capability of reduction of nitrate and nitrite. However, if one desires a reducing system which is specific to nitrite only, it has been found that a weakly acidic solution of iodide ion will work for this reaction which can be run under much more mild conditions. In particular, a solution of sodium iodide in glacial acetic acid.

For purposes of succinctness hereinafter, these three reducing systems will be referred to as the "transition metal systems", the "hydroquinone system" and the "iodide system". If one desires for whatever reason to distinguish between nitrate and nitrite in the process of this invention, one may first run the sample through the iodide system and this will allow determination of nitrite without nitrate, since this system is not sufficiently strong to reduce the nitrate. Thereafter, either one of the transition metal reducing systems or the hydroquinone reducing system can be employed to determine the nitrate content.

The amount or concentrations of the chemicals required in each of the reduction systems mentioned herein is not critical and it is well within the experimental skill of one in the art. The amount and concentrations can be varied, depending upon the volume and nature of the sample to be analyzed. However, some guidelines can be provided.

Turning first to the ferrous ion in the presence of the molybdenum VI catalyst, the concentrations of the ingredients are not critical. However, it has been found satisfactory that when using a 5 milliliter sample, one can use 5 milliliters of concentrated sulfuric acid, one milliliter of a 4% (weight to volume percentage) ferrous ammonium sulfate solution, and 1 milliliter of a 2% (weight to volume) of ammonium molybdate. The ferrous salt reduces the molybdenum (VI) to molybdenum (V) and the molybdenum (V) in turn causes the nitrate reduction. Generally, one may use from 100 to 1,000 times a molar excess of the ferrous ion and the molybdate salt over the nitrate being tested. The anion employed for the iron salt is not critical as long as it is not nitrate. With respect to the molybdate salt, ammonium molybdate may be used. Sodium molybdate will provide equally satisfactory results. Based on the size of sample mentioned herein, the amount of ferrous ammonium sulfate employed may vary from 0.05 grams to 2.0 grams, and the amount of molybdate salt from 0.1 grams to 2 grams. The concentration of acid may vary on a volume basis from 25% up to pure concentrated sulfuric acid.

Turning next to the titanium reducing agent, satisfactory results have been found when using 5 milliliter water samples by employing 5 milliliters of concentrated sulfuric acid and 1 milliliter of 5% titanium chloride. Here again, the titanium chloride may vary from 0.5% up to 20% on a weight to volume basis. And, once again, the sulfuric acid concentration may vary from 25% on a volume ratio up to pure concentrated sulfuric acid.

For the determination of nitrite with the iodide ion system, low acidity allows for selectivity over nitrate. A solution of glacial acetic acid has been used successfully.

Other acids other than glacial acetic acid may be employed, the critical factor being that the acidity of the system must be lower than the PKA of nitrous acid, which is 3.6. However, acetic acid is the preferred one. As a general guideline, one may employ 3 milliliters of glacial acetic acid, 20 milliliters of the aqueous sample, and 1 milliliter of 0.2 molar sodium iodide. The amount of sodium iodide may vary from 0.05 molar up to 2 molar. Here again, it is not critical that the iodide salt be sodium iodide, just as long as it is a soluble iodide salt.

The chemical reactions involved in the reduction of both the nitrate and the nitrite are well known.

The reduction of the nitrite is by the following reaction:

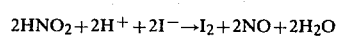

$$2HNO_2 + 2H^+ + 2I^- \rightarrow I_2 + 2NO + 2H_2O$$

The reduction of the nitrate is by the following reaction:

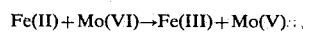

$$Fe(II) + Mo(VI) \rightarrow Fe(III) + Mo(V)$$

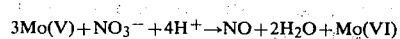

$$3Mo(V) + NO_3^- + 4H^+ \rightarrow NO + 2H_2O + Mo(VI)$$

As can be seen, the reactions for both nitrite and nitrate produce gas phase, nitric oxide. The nitric oxide must be stripped from the reduction reaction system. This can be most conveniently done by an inert gas such as nitrogen, helium, argon or the like. Very satisfactory results have been done with flushing with helium gas in a conventional degassing apparatus which sweeps away the nitric oxide for use in the chemiluminescence reaction with ozone.

The chemiluminescence reaction of nitric oxide with ozone is as follows:

$$NO + O_3 \rightarrow NO_2^* + O_2$$

$$NO_2^* \rightarrow NO_2 + h\nu$$

The chemiluminescence reaction is a known one. Basically, it is as follows: The nitric oxide and ozone are mixed in a reaction chamber to form metastable nitrogen dioxide which instantaneously decays to its ground state with a resulting photo-emission of light energy. The chemiluminescence detection is based on this photo-emission of light energy, and emitted light is detected by a photo-multiplier tube whose output is an electrical current proportionate to the intensity of the light detected. Appropriate electronic circuitry is provided in such detectors to convert the electrical current output of the photo-multiplier tube to an analog electrical signal fo driving a chart recorder and for application to an integrator for deriving and displaying a digital count that is proportional to the quantitative value of the nitrate-nitrite contained in the sample.

Numerous companies make such chemiluminescent detectors and most would be suitable for use in the present invention. For further details with regard to chemiluminescence detection systems, see U.S. Pat. No. 4,018,562 issued Apr. 19, 1977, which describes in detail such a detector. The description of said patent as it relates to detectors in general is hereby incorporated by reference.

Detectors such as a Bendix Model 8101-B Analyzer may be employed. Further details with regard to the mode of operation of a nitric oxide analyzer via chemiluminescence, may also be found in the Operations Service Manual for the Bendix 8101-B, Code No. B1357TM473, which is incorporated herein by reference. Other analyzers can also be used such as those made by Waters, Hewlett-Packard, and Columbia Instruments.

EXAMPLES

In the examples discussed below, the reagent systems used, particularly for the reducing reagents, were the following.

First, with respect to control systems of nitrate and nitrite which were tested.

Anhydrous potassium nitrate (J. T. Baker Chemical Co.) and sodium nitrite (J. T. Baker Chemical Co.) were used to prepare standard solutions of the respective anions. For nitrate determinations, solutions of reagent grade 4% ferrous ammonium sulfate and 2% ammonium molybdate (Matheson, Coleman and Bell Chemical Co.) in water were prepared daily. Titanium trichloride (technical grade) was purchased as a 20% solution from J. T. Baker Chemical Co. and diluted to 5% for use. Concentrated sulfuric acid was obtained from J. T. Baker Chemical Co.

For nitrite, 0.2 M sodium iodide (Matheson, Coleman and Bell Chemical Co.) and glacial acetic acid (J. T. Baker Chemical Co.) were used to provide the proper reducing conditions. For both methods, high purity water was obtained by passing distilled water through two IWT Research Model 1 ion-exchange columns connected in series (Illinois Water Treatment Co.).

The general procedures conducted for determination of nitrate and nitrite were employed as previously described and as specifically set forth hereafter. First, for nitrite:

A 20-mL aqueous sample, containing not more than 1.5 ug of nitrite, was placed in the reaction vessel. Added to this was 1 mL of 0.2 M NaI and 3 mL of glacial acetic acid. The reaction vessel was placed in a degassing apparatus and the nitric oxide swept into the chemiluminescence analyzer. Quantitative evaluation of samples was obtained by comparison with standards on the basis of peak areas.

Turning now to nitrate: For nitrate determinations, a 5-mL sample containing not more than 1.25 ug of nitrate was used. Added to this, in order, were 5 mL of concentrated $H_2SO_4$ and 1 mL of 2% ammonium molybdate. The nitric oxide produced was collected and measured as previously described. One milliliter of 5% titanium trichloride can be substituted for the ferrous ammonium sulfate and ammonium molybdate reagents.

Solutions of various amounts of nitrate and nitrite were prepared and analyzed for nitrate and nitrite as presented in Table I. Nitrite values were obtained using selective iodide reduction. Total nitrate-nitrite content was determined using the stronger reducing systems and conditions and nitrate was calculated by difference. The total amount of nitrate and nitrite found experimentally was within 3% of the calculated amount of nitrate-nitrite present, showing that both species are reduced to nitric oxide under these conditions.

TABLE I

| DETERMINATION OF NITRITE AND NITRATE | | | | |
|---|---|---|---|---|
| nitrate concn, mg $NO_3$—N/L | nitrite concn, mg $NO_2$—N/L | nitrite determined, mg $NO_2$—N/L | total $NO_2$/$NO_3$ determined, mg $NO_2$—$NO_3$—N/L | nitrate by difference, mg $NO_3$—N/L |
| 0.00300 | 0.00300 | 0.00300 | 0.00635 | 0.00335 |
| 0.00600 | 0.00600 | 0.00608 | 0.0128 | 0.00672 |
| 0.0120 | 0.0120 | 0.0122 | 0.0241 | 0.0119 |
| 0.0240 | 0.0240 | 0.0242 | 0.0488 | 0.0246 |

URINE AND BLOOD ANALYSIS

Recovery data for nitrate added to urine are reported in Table II. Nitrate was determined in three urine samples followed by addition of 2.5 to 20 ug of nitrate to 1.0 mL of urine. The total amount of nitrate was then determined and net and percent recoveries calculated. Percent recovery ranged from 97 to 103 percent.

Recovery of nitrate added to blood plasma and whole blood is reported in Tables III and IV, respectively. Nitrate was added to 0.5 mL samples of whole blood or plasma which were then deproteinized and analyzed for total nitrate present. Recoveries of nitrate added to blood plasma in the range of 500 to 5000 ng per 0.5 mL sample were 88 to 97 percent.

TABLE II

RECOVERY OF NITRATE ADDED TO URINE

| INITIAL CONCENTRATION ($\mu$g NO$_3$—N/mL) | NITRATE ADDED ($\mu$g NO$_3$—N/ 1 mL urine) | TOTAL NITRATE RECOVERED ($\mu$g NO$_3$—N) | NET NITRATE RECOVERED ($\mu$g NO$_3$—N) | PERCENT RECOVERY (%) |
|---|---|---|---|---|
| MEAN ± SD (% CV) | | MEAN ± SD (% CV) | MEAN ± D (% RD) | MEAN ± D (% RD) |
| 6.69 ± 0.07 (1) | — | 6.69 ± 0.07 (1) | — | — |
| 6.69 ± 0.07 (1) | 2.50 | 9.15 ± 0.06 (0.7) | 2.46 ± 0.09 (4) | 98 ± 4 (4) |
| 6.69 ± 0.07 (1) | 5.00 | 11.5 ± 0.1 (0.9) | 4.8 ± 0.1 (2) | 97 ± 2 (2) |
| 6.69 ± 0.07 (1) | 10.0 | 16.8 ± 0.3 (2) | 10.2 ± 0.3 (3) | 102 ± 3 (3) |
| 8.6 ± 0.1 (1) | — | 8.6 ± 0.1 (1) | — | — |
| 8.6 ± 0.1 (1) | 5.00 | 13.5 ± 0.1 (0.7) | 4.9 ± 0.1 (2) | 97 ± 2 (2) |
| 8.6 ± 0.1 (1) | 20.0 | 29.1 ± 0.4 (1) | 20.6 ± 0.4 (2) | 103 ± 2 (2) |
| 16.9 ± 0.4 (2) | — | 16.9 ± 0.4 (2) | — | — |
| 16.9 ± 0.4 (2) | 10.0 | 27 ± 1 (4) | 10. ± 1 (10) | 100 ± 10 (10) |
| 16.9 ± 0.4 (2) | 15.0 | 31.5 ± 0.6 (2) | 14.6 ± 0.7 (5) | 97 ± 5 (5) |

TABLE III

RECOVERY OF NITRATE ADDED TO BLOOD PLASMA

| INITIAL CONCENTRATION (ng NO$_3$—N/mL) | NITRATE ADDED (ng NO$_3$—N/ 0.5 mL Blood) | TOTAL NITRATE RECOVERED (ng NO$_3$—N) | NET NITRATE RECOVERED (ng NO$_3$—N) | PERCENT RECOVERY (%) |
|---|---|---|---|---|
| MEAN ± SD (% CV) | | MEAN ± SD (% CV) | MEAN ± D (% RD) | MEAN ± D (% RD) |
| 910 ± 20 (2) | — | 450 ± 10 (2) | — | — |
| 910 ± 20 (2) | 600. | 893 ± 5 (0.6) | 440 ± 10 (2) | 88 ± 2 (2) |
| 910 ± 20 (2) | 1000. | 1360 ± 20 (1) | 900 ± 20 (2) | 90 ± 2 (2) |
| 910 ± 20 (2) | 2000. | 2300 ± 3 (0.1) | 1980 ± 10 (0.5) | 97 ± 1 (1) |
| 910 ± 20 (2) | 5000. | 5222 ± 10 (0.2) | 4770 ± 10 (0.2) | 95 ± 1 (1) |

TABLE IV

RECOVERY OF NITRATE ADDED TO WHOLE BLOOD

| INITIAL CONCENTRATION (ng NO$_3$—N/mL) | NITRATE ADDED (ng NO$_3$—N/ 0.5 mL Blood) | TOTAL NITRATE RECOVERED (ng NO$_3$—N) | NET NITRATE RECOVERED (ng NO$_3$—N) | PERCENT RECOVERY (%) |
|---|---|---|---|---|
| MEAN ± SD (% CV) | | MEAN ± SD (% CV) | MEAN ± SD (% RD) | MEAN ± SD (% RD) |
| 720 ± 20 (3) | — | 359 ± 7 (2) | — | — |
| 720 ± 20 (3) | 250. | 574 ± 9 (2) | 220 ± 10 (5) | 90 ± 4 (5) |
| 720 ± 20 (3) | 500. | 796 ± 9 (0.3) | 437 ± 7 (2) | 88 ± 2 (2) |
| 720 ± 20 (3) | 1000. | 1300 ± 2 (0.3) | 941 ± 7 (0.7) | 94 ± 1 (1) |
| 720 ± 20 (3) | 2000. | 2382 ± 8 (0.3) | 2020 ± 10 (0.5) | 101 ± 1 (1) |
| 720 ± 20 (3) | 5000. | 5320 ± 20 (0.4) | 4960 ± 20 (0.4) | 99 ± 1 (1) |

In summary, it can be seen that a highly useful, selective, sensitive and speedy technique has been developed. The reduction reactions generally take a minute or less, and the chemiluminescence reaction is very quick. As a result, the detection is extremely sensitive, selective to nitrate and nitrite, and even distinguishes between the two if the iodide reaction is run first. Moreover, it works for biological fluids. Color and turbidity do not interfere. Also, a minimum of interferring ions have been found. Finally, the system successfully determines nitrate and nitrite as opposed to determining total nitrogen content.

What is claimed is:

1. A method of selective determination of nitrite content of a test sample containing nitrite, and nitrate, and thereafter determining nitrate content of said sample, without also determining additional nitrogen content, said method comprising:
   solubilizing a test sample containing nitrite and nitrate,
   reducing the nitrite content of said sample with a weakly acidic solution of a water soluble iodide salt to produce nitric oxide, without also reducing the nitrate content,
   stripping said nitric oxide from the reduction reaction mixture,
   reacting said nitric oxide with ozone in a chemiluminescence reaction, and
   determining the magnitude of the chemiluminescence reaction to indicate the nitrite content of said sample, and thereafter,
   reducing the nitrate content of said sample with a strongly acidic solution of a transition metal reducing system selected from the group of ferrous ion in the presence of molybdenum ion, or titanium ion, to produce nitric oxide, without also reducing additional nitrogen content,
   stripping said nitric oxide from the reduction reaction mixture,
   reacting said nitric oxide with ozone in a chemiluminescence reaction, and
   determining the magnitude of the chemiluminescence reaction to indicate the nitrate content of said sample.

2. The method of claim 1 wherein said nitric oxide produced in said reducing step is stripped from said sample by inert gas sweeping.

3. The method of claim 2 wherein said inert gas is helium.

4. The method of claim 2 wherein said weakly acetic solution is an acetic acid solution, and said water soluble iodide salt is sodium iodide.

* * * * *